United States Patent
Krzysik et al.

(10) Patent No.: US 11,801,215 B2
(45) Date of Patent: Oct. 31, 2023

(54) HAIR CARE COMPOSITIONS AND METHODS

(71) Applicant: Innospec Limited, Cheshire (GB)

(72) Inventors: Duane Krzysik, Salisbury, NC (US); Robert Griffiths, Charlotte, NC (US)

(73) Assignee: Innospec, Ltd., Ellesmere Port (GB)

( * ) Notice: Subject to any disclaimer, the term of this patent is extended or adjusted under 35 U.S.C. 154(b) by 27 days.

(21) Appl. No.: 16/645,138

(22) PCT Filed: Aug. 24, 2018

(86) PCT No.: PCT/US2018/047911
§ 371 (c)(1),
(2) Date: Mar. 6, 2020

(87) PCT Pub. No.: WO2019/060089
PCT Pub. Date: Mar. 28, 2019

(65) Prior Publication Data
US 2020/0261349 A1    Aug. 20, 2020

Related U.S. Application Data

(60) Provisional application No. 62/562,653, filed on Sep. 25, 2017.

(51) Int. Cl.
| | | |
|---|---|---|
| *A61K 8/898* | (2006.01) | |
| *A61K 8/06* | (2006.01) | |
| *A61K 8/86* | (2006.01) | |
| *A61Q 5/12* | (2006.01) | |
| *C08G 77/26* | (2006.01) | |
| *C08G 77/388* | (2006.01) | |
| *C08L 83/08* | (2006.01) | |

(52) U.S. Cl.
CPC ............. *A61K 8/898* (2013.01); *A61K 8/06* (2013.01); *A61K 8/86* (2013.01); *A61Q 5/12* (2013.01); *C08G 77/26* (2013.01); *C08G 77/388* (2013.01); *C08L 83/08* (2013.01)

(58) Field of Classification Search
USPC .......................................... 424/70.12, 70.122
See application file for complete search history.

(56) References Cited

U.S. PATENT DOCUMENTS

| | | | | |
|---|---|---|---|---|
| 5,540,952 A | * | 7/1996 | Canivenc .......... | D06M 15/6436 427/392 |
| 6,605,577 B1 | | 8/2003 | Harrison et al. | |
| 6,709,648 B2 | | 3/2004 | Sako et al. | |
| 8,097,602 B1 | | 1/2012 | Holzer | |
| 8,329,307 B2 | * | 12/2012 | Pouchelon ......... | D06M 15/643 524/588 |
| 2003/0134760 A1 | | 7/2003 | Harrison et al. | |
| 2006/0057217 A1 | | 3/2006 | Utschig et al. | |
| 2009/0004123 A1 | * | 1/2009 | Manuszak ............ | A61K 8/898 424/59 |
| 2009/0110703 A1 | * | 4/2009 | Tolla .................. | A61Q 3/00 424/59 |
| 2011/0052523 A1 | * | 3/2011 | Moriya ............... | A61K 8/27 556/424 |
| 2011/0110991 A1 | | 5/2011 | Garrison et al. | |
| 2011/0110992 A1 | | 5/2011 | Garrison et al. | |
| 2012/0021025 A1 | | 1/2012 | Bendejacq et al. | |
| 2013/0034515 A1 | | 2/2013 | Stone et al. | |
| 2013/0243704 A1 | * | 9/2013 | Manuszak ............ | A61Q 5/12 424/59 |
| 2014/0308227 A1 | | 10/2014 | Mabille | |
| 2016/0228342 A1 | * | 8/2016 | Rose .................. | A61Q 5/12 |
| 2016/0271023 A1 | | 9/2016 | Bekemeier et al. | |
| 2016/0310404 A1 | | 10/2016 | Schrott et al. | |
| 2017/0189313 A1 | | 7/2017 | Tan et al. | |

FOREIGN PATENT DOCUMENTS

| | | |
|---|---|---|
| DE | 102011087975 A1 | 6/2013 |
| JP | 2009096736 A | 5/2009 |
| JP | 2011-105631 A | 6/2011 |
| JP | 2012-092040 A | 5/2012 |
| WO | 2016164292 A1 | 10/2016 |

OTHER PUBLICATIONS

English language translation JP 2005-132779, May 2005.*
International Search Report application No. PCT/US18/47875, dated Nov. 26, 2018.
International Search Report application No. PCT/US18/47911, dated Nov. 7, 2018.
"One Week Straightener", ID 573472, Database GNPD (Online), MINTEL, Aug. 2006.
"Straight Away Conditioner", ID 2452005, Database GNPD (Online), MINTEL, Jun. 2014.
"Anti-Frizz Serum", ID 707129, Database GNPD (Online), MINTEL, May 2007.
"Innospec—Inner Beauty—Product Guide." Feb. 28, 2017. https://customchemicalservices.com/wp-content/uploads/2017/02/INN15006_Product_Guide_FINAL.pdf.

(Continued)

*Primary Examiner* — Margaret G Moore (74) *Attorney, Agent, or Firm* — Carlos A. Fisher; Stout, Uxa & Buyan, LLP (57) ABSTRACT

Methods and compositions for preventing or reducing hair frizz. The compositions are anhydrous and comprise at least one polysiloxane fluid component selected from an amodimethicone and a polysiloxane component comprising a plurality of hindered amine side chains. The compositions also comprise a silicone-compatible, volatile liquid carrier component, preferably selected from a low molecular weight, volatile siloxy component; a hydrocarbon; and an alcohol. The compositions are preferably serums or fluids, and are suitable for use in a conditioner, as a "leave-in" hair care product, or as a touch-up hair care product suitable for use during the day.

17 Claims, 1 Drawing Sheet

(56) References Cited

OTHER PUBLICATIONS

Product Information—Microsil@ Finish. Nov. 30, 2015. https://www.asharrison.com.au/wp-content/uploads/2015/11/Microsil®-Finish.pdf.
Office Action dated Jul. 26, 2022 in related Japanese Patent Application No. 2020-517159.
Office Action dated Aug. 9, 2022 in related Japanese Patent Application No. 2020-517191.
Written Opinion dated Jul. 24, 2022 in related Singapore Patent Application No. 11202002414S.
Written Opinion dated Jul. 24, 2022 in related Singapore Patent Application No. 11202002377U.
Office Action dated Jul. 5, 2022 in related Chinese Patent Application No. 201880062383.1.

* cited by examiner

HAIR CARE COMPOSITIONS AND METHODS

CROSS-REFERENCES TO OTHER RELATED PATENT APPLICATIONS

This application claims the benefit of U.S. provisional patent application Ser. No. 62/562,653, filed Sep. 25, 2017, which is hereby incorporated by reference herein in its entirety.

FIELD OF THE INVENTION

The present invention concerns compositions and methods for reducing and preventing frizzy hair. Such compositions may comprise and/or be comprised in hair care products including, without limitation, shampoos, conditioners, styling gels, creams, serums, sprays, and liquids, and restorative hair care products. Preferably, the compositions of the invention may be used primarily or substantially solely as an anti-frizz hair treatment, particularly, though not solely, as a composition to be left in the hair for an extended time (herein termed a "leave-in" or "leave-on" hair care product). In other examples the compositions of the invention may be a component of a multi-purpose hair care composition.

BACKGROUND

Hair frizz is a problem that commonly occurs in all hair types, especially to people who have wavy and curly hair, particularly when humidity levels and/or dew points are high; this typically occurs in the summer months and at tropical latitudes. However, relative humidity, the ratio of the partial pressure of water vapor to the equilibrium vapor pressure of water at a given temperature, depends on both temperature and the local air pressure, and high relative humidity can be attained at low temperatures with comparatively little water vapor. Thus, depending upon local air pressure, in some cases relative humidity greater than only about 50% can be considered sufficiently high humidity to cause hair frizz.

What is normally thought of as "hair" (i.e., the hair shaft, external to the hair root under the skin) is comprised of keratin, a protein in which disulfide bonds hold the strands together. The hair shaft comprises three layers: the medulla, the cortex and the cuticle. The medulla is a thin core of transparent cells and air spaces. The cortex forms the bulk of the hair shaft and usually contains pigment and long keratin filaments, which are held together by disulfide and hydrogen bonds.

The cuticle is a protective layer comprised of overlapping cells, organized like fish scales facing downwards. The outer cuticle holds the hair shaft in the hair follicle by means of a bond. When it is healthy, it also minimizes the movement of water (moisture) in and out of the underlying cortex. However, chemical processes and weathering can lift the cuticle from the cortex and disrupt this balance.

When high humidity causes frizz, the cuticle layer of hair is raised. The hair cuticles normally regulate the water absorption in the hair. Raised cuticles occur in the areas of naturally curly hair in which there is a bend in the curl and permit moisture to be absorbed by the hair cortex. As a result, the hair may appear dry (because the cuticle may indeed be dry); the hair shaft increases in volume due to the water uptake by the cortex causing the hair to swell. In general, extremely wavy and curly hair tends to have more frizz than straight hair because the hair does not properly regulate the amount of water absorbed by the hair.

In addition to curly or wavy hair, hair that has been damaged by chemical processing (such as straightening, permanent waving, hair dyeing or bleaching), heat (such as by blow drying and the use of flat irons or curling irons), mechanical damage (such as by excessive combing and brushing) and environmental damage (such as sunlight, air or water pollution, chlorine, etc.) causes cuticle damage, permitting water to enter the cortex and the hair to absorb more moisture.

Throughout history natural oils have been used to control fizz. Some common natural oils include almond, olive, coconut, moringa, avocado, shea butter, argan, sunflower oil, etc. Additionally, mineral oil and fats have been used. However, oils tend to make the hair look wet, leave the hair greasy and oily to the touch, and to transfer easily to bedding and clothes.

More recently, various conditioners and "leave-in" products have been formulated to control frizz. These products generally fall into four categories:

a) Styling products, like gels, creams, hair mousse and hair spray to help keep the hair in place. However, organic styling resins such as these cause the hair to feel unnatural and stiff.

b) Water and alcohol-based products containing fatty quaternary ammonium components, fatty alcohols and natural or petroleum-based oils. These may also contain some amounts of cyclomethicone and dimethicone to improve the distribution of the product through the hair, improve combing, improve styling process and impart a dry hair feel to the hair.

c) Alcohol-based serums and sprays containing cyclomethicones, dimethicones and alkyl modified silicones. In these products the volatile component (which may comprise ingredients such as ethanol and volatile silicones) help to dehydrate the hair cortex, and after evaporation of the volatile components a film of the non-volatile silicones and other components forms on the cuticle to seal the hair from moisture.

d) Silicone serums containing cyclomethicones, dimethicones and significant concentrations of high molecular weight and/or high viscosity silicones, such as dimethicone gum and dimethiconol gum. As in the alcohol-base serums and sprays, in these products the low molecular weight, volatile silicone helps to replace moisture from the hair, evaporates after application, and leaves a film of the high molecular weight non-volatile silicone on the hair to seal the hair from moisture. Typical serum formulations have a viscosity ranging from about 500 cps to about 5,000 cps.

Song et al., U.S. 2016/0374932 and WO 2015/200778 describe a composition comprising an amodimethicone/morpholinomethyl silsesquioxane copolymer made by emulsionpolymerization in water.

Uehara et al., WO2004/030646 discloses a composition comprising a mixture of high, medium, and low viscosity silicones; an amidoamine; an acid; a high melting point fatty compound and water.

Richards, WO2010/003793 discloses an aqueous composition comprising three kinds of silicones: an alkyl modified silicone, a second silicone comprising, for example, a polydimethylsiloxane gum, and a functionalized silicone such as an amino-functionalized silicone (e.g., an amodimethicone).

Scholz, US2002/0197227 discloses a hair care composition comprising: a high viscosity silicone polymer, a non-volatile carrier fluid and volatile silicone based carrier fluid.

Garrison et al, US2011/0110991 discloses a composition comprising a hydrophobic particulate material, a silicone-based hydrophobic film former and a volatile hydrocarbon or silicone fluid.

Singer et al., U.S. Pat. No. 8,591,872 discloses a composition comprising, in a cosmetically acceptable carrier, the following ingredients: at least one non-hydroxide base chosen from monoethanolamine, triethanolamine and ethylenediamine; one or more protein denaturants such as urea and/or hydroxyethylurea; an alkoxysilane; and optionally at least one fatty substance.

These products perform with varying degrees of efficacy, and many users of these products are not satisfied with the limited degree of frizz control that the above technologies provide.

Therefore there is a need for high performance frizz control products particularly, but not exclusively, in "leave-in" formulations that are acceptable to the consumer. Such a formulation would ideally provide good application feel (without heaviness, stiffness, greasiness or a "watery" feel), a good ability to be smoothly distributed and spread on the hair and, when dry, such a formulation would ideally leave the hair manageable, and feeling and looking natural. Other formulations that contain the anti-frizz components of the present invention may comprise hair conditioners, such as a conditioner improving the ability of wet or dry hair to be combed.

SUMMARY OF THE INVENTION

The present invention is directed to compositions for reducing or eliminating frizz from hair, such compositions having good application feel (a good ability to be smoothly distributed and spread on the hair and, when dry, to leave the hair manageable), and methods for making and using such compositions.

According to one embodiment, there is provided a flowable composition comprising:
  a) 2% or more by weight, of a polysiloxane fluid component comprising an alkoxytetramethyl piperidinyl dimethicone component and
  b) a silicone-compatible, volatile liquid carrier component.

According to a second embodiment, there is provided a flowable composition comprising:
  a) 2% or more, by weight, of a polysiloxane fluid component comprising an propoxytetramethyl piperidinyl dimethicone component and
  b) a silicone-compatible, volatile liquid carrier component.

According to a third embodiment, there is provided a flowable composition comprising:
  a) 2% or more, by weight, of a polysiloxane fluid component comprising a trimethylsilyl siloxane component and
  b) a silicone-compatible, volatile liquid carrier component.

According to a fourth embodiment, there is provided a flowable composition comprising:
  a) 2% or more, by weight, of a polysiloxane fluid component comprising an aminopropyl siloxane component and
  b) a silicone-compatible, volatile liquid carrier component.

According to a fifth embodiment, there is provided a flowable composition comprising:
  a) 2% or more, by weight, of a polysiloxane fluid component selected from one or more of:
    i) an amodimethicone component, and
    ii) a polysiloxane component comprising a plurality of hindered amine side chains; and
  b) a silicone-compatible, volatile liquid carrier component.

According to a sixth embodiment, there is provided a flowable composition comprising:
  a) 2% or more, by weight, of a polysiloxane fluid component comprising the structure wherein X+Y is between about 50 to about 500 and R is a $C_3$ to $C_5$ alkylene group; and
  b) a silicone-compatible, volatile liquid carrier component.

According to a seventh embodiment, there is provided a flowable composition comprising:
  a) 2% or more, by weight, of a polysiloxane fluid component comprising an aminopropyl dimethicone; and
  b) a silicone-compatible, volatile liquid carrier component.

According to an eighth embodiment there is provided a method of reducing or preventing hair frizz, comprising the steps:
  I) applying to hair a composition of any of the first through seventh embodiments; and
  II) distributing said composition along a plurality of hair shafts.

According to a ninth embodiment there is provided a method of increasing curl memory, comprising the steps:
  I) applying to hair a composition of any of the first through seventh embodiments; and
  II) distributing said composition along a plurality of hair shafts.

According to a tenth embodiment there is provided the use of a composition of any of the first through seventh embodiments to reduce hair frizz.

According to a eleventh embodiment there is provided the use of a composition of any of the first through seventh embodiments to reduce hair frizz by more than 80% when held at 80° F. and 80% humidity, as compared to substantially identical hair not treated with said composition, but otherwise handled identically.

According to a twelfth embodiment there is provided the use of a composition of any of the first through seventh embodiments to increase curl memory, as compared to substantially identical hair not treated with said composition but otherwise handled identically.

According to a thirteenth embodiment there is provided the composition of any of the first through seventh embodiments which is anhydrous.

According to a fourteenth embodiment there is provided the method or use of any of the eighth through twelfth embodiments to reduce hair frizz, in which the composition is anhydrous.

The invention is not limited to the embodiments described above, and additional embodiments are disclosed in the disclosure of the specification.

The combination of amino-substituted polysiloxane fluid components as described herein at concentrations at or above 2% by weight, or at or above about 2.1% by weight, or at or above about 2.2% by weight, or at or above about 2.3% by weight, or at or above about 2.4% by weight, about 2.5% by weight, with one or more silicone-compatible, non-aqueous volatile carriers has been found to solve the problem of providing a reduction in hair frizz greater that 50%, or greater than 60%, or greater than 70%, or greater than 80%, or greater than 85% as compared to identical and otherwise identically-treated hair not contacted with said composition.

The methods and compositions disclosed herein may be used on hair that has not been artificially colored (e.g., dyed, bleached, or pigmented), or on hair that has been artificially colored.

In some embodiments the invention is drawn to a use of a composition of the first through seventh and thirteenth embodiments comprising:
 a) at least about 2%, by weight, of a polysiloxane fluid component selected from one or more of:
  i) an amodimethicone component, and
  ii) a polysiloxane component comprising a plurality of hindered amine side chains;
 b) a silicone-compatible, volatile liquid carrier component to treat hair that has been artificially colored to retain its color, as compared to otherwise identical colored hair not treated with such a composition.

In some embodiments the invention is drawn to a use of a composition of the first through seventh and thirteenth embodiments comprising:
 a) at least about 2%, by weight, of a polysiloxane fluid component selected from one or more of:
  i) an amodimethicone component, and
  ii) a polysiloxane component comprising a plurality of hindered amine side chains; and
 b) a silicone-compatible, volatile liquid carrier component to increase curl retention and/or curl memory properties of hair treated with the composition, as compared to identical and otherwise identically-treated hair not treated with said composition.

In a further embodiment, the compositions containing amino-substituted polysiloxanes at concentrations at or above 2.5% by weight, with one or more silicone-compatible, non-aqueous volatile carriers and a dimethicone or dimethiconol component with a viscosity of greater than 150,000 cSt at a concentration of above 5% by weight and/or a trimethylsiloxy-silicate at above 5% weight provide a significant reduction in hair fizz, as measured according to the procedures set forth under the heading High Humidity Frizz Control Test Method (see Examples section below) and additionally provide curl retention and curl memory properties (as measured according to the procedures set forth in e.g., Example 10, below), compared with untreated otherwise identical hair under the same test conditions.

Various suitable methods for determining frizz reduction are available in the art. A preferred method is detailed below under the heading High Humidity Frizz Control Test Method; see Examples section below.

As used herein, viscosity of a fluid may be expressed as centipoise (cP) or centistokes (cSt), wherein cSt=cP divided by the specific gravity (SG) of the fluid. Generally, the viscosity of components are expressed in cSt and the viscosity of formulations are expressed in cP. Where no temperature is referred to, viscosity is measured at 25° C.

As used herein, the expression "at least one" means one or more, and thus includes individual components as well as mixtures and/or combinations of components.

As used herein, the words "a" and "an" means one or more, and thus includes individual components as well as mixtures and/or combinations of components.

As used herein, the term "about" means plus or minus 10%, or plus or minus 15%, of the indicated number.

As used herein, the term "hair" means keratinous fibers. As used, the term "hair" may include "living" hair, i.e. on a living body, or may be "non-living" i.e. in a wig, hairpiece or other aggregation of non-living fibers, such as those used in textiles and fabrics. Mammalian hair, e.g. human hair, is preferred in various embodiments. However animal hair (such as dog or horse), wool, fur and other keratinous fibers are suitable for use in the methods and with the compositions described herein.

The tem "anhydrous" as used herein is intended to mean that the composition is either completely free of unbound water or contains only trace amounts of unbound water, such as, for example, no more than about 1% by weight, such as no more than about 0.5% by weight, based on the weight of the composition.

As used herein, the phrase "minimizing damage" to the hair and/or skin is intended to mean that the breakage of the hair has been reduced or eliminated and/or the skin is substantially not irritated by exposure for 15 minutes, followed by rinsing with water.

As used herein, the term "ready-to-use composition" means a composition intended to be applied in unmodified form to the keratin fibers, i.e. it may be stored in unmodified form before use or may result from the extemporaneous mixing of two or more compositions.

As used herein, the term "applying" a composition to the hair or "treating" the hair with a composition is intended to mean contacting and distributing a hair care composition on the hair.

As used herein, "cosmetically acceptable" means that the item in question is compatible with human or animal skin or hair.

As used herein, "cosmetically acceptable carrier" means a carrier that is compatible with human or animal skin or hair and feels pleasant with no adverse odor.

As used herein, "conditioning" means imparting to at least one keratinous fiber at least one property chosen from "combability" (the ability of wet or dry hair to be combed easily), manageability, shine, and softness.

As used herein, "curl definition" refers to curly hair tresses in which the individual hairs align with each other to a sufficient degree to render a discernible curl shape to the tress as a whole.

As used herein "curl memory" refers to curly hair tresses in which a curl snaps back into its original shape after the curl is stretched and released.

As used herein "curl fatigue" means that a curl having initial curl memory does not snap back into its original shape after the curl is stretched and released more than about three times.

As used herein "lack of curl fatigue" means that a curl having initial curl memory continues to snap back into its original shape after the curl is stretched and released more than about three times.

As used herein, "curl retention" means the ability of hair having a defined curl, or induced to have a defined curl, to have curl memory when the hair is treated with a composition as compared to untreated, otherwise identical hair.

As used herein, "silicone-compatible" means silicone-miscible.

As used herein, the term "frizz" or "frizzy" hair means short strands sticking up (for example where the hair is parted or elsewhere along the hair length) and projecting away from the main body of hair; this type is especially noticeable on women with straight hair who are trying to achieve a smooth style. Additionally, "frizz" may be used to refer to strands of wavy or curly hair that do not align with others to form a defined wave or curl.

As used herein the term "flowable" means non-solid, substantially fluid, and having the property of changing its shape at a relatively steady rate when acted upon by a force.

As used herein the term "permitted to dry", with respect to hair, means allowing volatile components applied to the hair to evaporate to the point that an ordinary person would consider the hair dry to the touch.

As used herein, the term "volatile" means that at least about 60% by weight of a component evaporates at temperature of about 40° C. at a pressure of about 100 kPa (1 bar) within a time period of about 100 minutes.

As used herein, the terms "improved shine", "enhanced shine", and similar terms relating to increased shine means that untreated hair, treated with one or more compounds, displays subjectively or semi-objectively using photography image analysis techniques an increase in the reflection of light (e.g. increased gloss and sheen) as compared to identical or similar hair untreated with the same compound or compounds.

As used herein the term "dimethicone" means an optionally substituted polydimethylsiloxane (PDMS) comprising M siloxide units ((CH$_3$)$_3$SiO—) at its ends. Additionally, unless indicated otherwise in this specification or the claims, as used herein a "dimethicone" may also refer to a cyclomethicone, having the formula [(CH$_3$)$_2$SiO$_n$].

As used herein, the term "dimethiconol" means an optionally substituted polydimethylsiloxane having a hydroxyl group, rather than a methyl group, at each end.

Unless otherwise indicated, each and every range of values (concentrations, viscosities, and the like) stated in this specification, including the claims, are intended to specifically include the entire range and not just the endpoint(s). For example, a range stated to be 0 to 10 is intended to disclose all whole numbers between 0 and 10 such as, for example 1, 2, 3, 4, etc., all fractional numbers between 0 and 10 to three significant figures, for example 1.5, 2.3, 4.57, etc., and the endpoints 0 and 10. Also, a range associated with chemical substituent groups such as, for example, "C$_1$ to C$_5$ hydrocarbons", is intended to specifically include and disclose C$_1$ and C$_5$ hydrocarbons as well as C$_2$, C$_3$, and C$_4$ hydrocarbons.

As is described herein, polysiloxanes may be used in the compositions of the invention.

These include such compounds as dimethicone and dimethiconol, which differ by their end caps, wherein:

n and m are each 1 or more, and wherein the structure is dimethicone when R=CH$_3$ and the structure is dimethiconol when R=OH. Viscosity increases with increasing chain length, with a preferred range of viscosities ranging from about 0.65 cSt to >3 million cSt.

Unless otherwise indicated, a dimethiconol having an otherwise identical or substantially identical structure as a given dimethicone may be substituted for the given dimethicone in the compositions of the present invention, and vice versa.

Dimethicones, dimethiconols and their derivatives may have various or multiple functions in the compositions disclosed herein.

As carrier components; the volatile, low viscosity dimethicone(s), dimethiconol(s), phenyl silicone(s, or derivative(s) thereof may impart spreadability without a greasy or waxy feeling. Such compounds may include, or be selected from a trisiloxane, a tetrasiloxane and a pentasiloxane, including linear, cyclic, and phenyl derivatives thereof, and may include low molecular weight dimethicone, contained in preparations such as (identified by their viscosities): 1 cSt, 1.5 cSt, 2 cSt, and as impurities in non-homogeneous siloxane preparations, such as dimethicone (5 cSt) and dimethicone (6 cSt). These may be used alone or in combination with one or more volatile hydrocarbon or alcohol.

Non-volatile, higher molecular weight polysiloxanes such as dimethicones, dimethiconols, and phenyl silicones, as well as derivatives and mixtures thereof, may be used in some embodiments of the present invention as additional frizz-reduction agents, hair shine components and aesthetic modifiers. Such components may be divided into "lower viscosity" (low molecular weight) siloxane components, for example having a viscosity of between 6 to 5000 cSt; "intermediate viscosity" (intermediate molecular weight) siloxane components, for example having a viscosity between 5000 to 60,000 cSt; and "high viscosity" (high molecular weight) siloxane component, for example having a viscosity >60,000 cSt. Moreover, siloxane components of differing molecular weight and/or structure may be mixed to achieve compositions having a desired viscosity, and/or balance of frizz reduction, hair shine, aesthetic desirability, and manageability. Furthermore, some polysiloxane derivatives may comprise co-polymers or cross-polymers with groups such as fatty acid containing moieties, alkenyl-containing moieties, and the like.

One or more additional components may be added to the compositions of the present invention. For example, such additives may, without limitation, include:

Colorants including, but not limited to, cosmetically approved silicone soluble dyes Hair shine ingredients, including but not limited to phenyltrimethicone, diphenylsiloxy phenyl trimethicone, diphenyl dimethicone, caprylic/capric triglycerides, mineral or natural oils, alkyl benzoates and the like. When oils or triglycerides are used in the present composition, their concentration is maintained low enough (e.g., less than about 10% or less than about 5% or less than about 2% or less than about 1.5%) to add shine to the hair without rendering the hair greasy or wet.

Sunscreen ingredients such as, without limitation, TiO$_2$ and zinc oxide to protect the hair from sunbleaching, discoloration or fading; such as for color-treated hair and to preserve hair color.

Aesthetic modifiers including, but not limited to, dimethicone crosspolymer, dimethicone/vinyl dimethicone crosspolymer, dimethicone/phenyl vinyl dimethicone crosspolymer, vinyl dimethicone/lauryl dimethicone crosspolymer, lauryl polydimethylsiloxyethyl dimethicone/bis-vinyl dimethicone crosspolymer, alkyl silicones, stearoxytrimethylsilane, ethylene-dimethicone copolymer, polyethylsiloxanes, alkyl silicones including caprylyl methicone, lauryl methicone and stearoxymethicone and the like.

Aesthetic modifiers may include thickener components, preservative components, fragrance components, pH adjustment components, plasticizer components, appearance modifiers or anti-oxidant components. Such aesthetic modifier components generally include ingredients which help to make delivery of the functional ingredients more acceptable by, for example, helping the active ingredients spread, diluting the active ingredients, stabilizing the active ingredients, and/or improving the look and feel of the composition when applied to the hair.

Other components effective in making the composition appealing to the consumer, such as (without limitation) essential oils, botanicals, scents, nucleic acids, specialty extracts, proteins, amino acids and vitamins. It will be apparent to the person of ordinary skill in the art in view of the present specification that low viscosity non-aerosol spray formulations of the present invention can also be applied as an aerosol using a propellant without loss of effectiveness. Additionally, while the compositions of the present invention are very preferably anhydrous, in other, currently less preferred, examples the anhydrous compositions of the present invention may also or alternatively be present in water-in-silicone and silicone-in-water emulsions as anti-frizz creams and/or lotions.

In some embodiments, such water-in-silicone or silicone-in-water emulsions can easily be made using the anhydrous compositions disclosed herein as a base, then mixing the base with an aqueous phase preferably containing one or more emulsifying and stabilizing surfactant and occasionally a salt, and forming an emulsion. The emulsion may be a regular emulsion, formed by thorough mixing of the phases, or may be a stable microemulsion appearing transparent or translucent. In certain cases, the refractive indices of the phases may be matched using a refractive index matching agent such as water or propylene glycol.

In other, less preferred, embodiments one or more of the components used in the anhydrous compositions of the present invention may instead be separately provided in a dispersion or emulsion comprising a silicone phase containing such component or components and an aqueous phase. Two or more such dispersions or emulsions may, under certain circumstances be combined and emulsified to create an emulsion equivalent to that created by using the preferred anhydrous compositions in the manner described above as a silicone phase "base" and mixing a water phase.

Thus, in certain embodiments the present invention may comprise an emulsion having a silicone phase, in which the silicone phase comprises
a) at least 2%, by weight, of a polysiloxane fluid component selected from one or more of:
i) an amodimethicone component, and
ii) a polysiloxane component comprising a plurality of hindered amine side chains; and
b) a silicone-compatible, volatile liquid carrier component.

In preferred, although non-exclusive, examples of the present invention, the composition of the present invention is a "leave-in" hair care product, which is applied to and left in the hair during the day or a part thereof. For example, the leave-in anti-frizz composition may be applied after shampooing the hair, and permitted to dry on the hair. In other leave-in applications the composition of the present invention may be sprayed or otherwise applied to the hair during the day as an aerosol or non-aerosol touch-up anti-frizz product.

The examples which follow are particular illustrations of the invention, which will be understood not to be limited thereby. The scope of the invention is defined solely by the claims.

DETAILED DESCRIPTION OF THE INVENTION

The present invention is drawn to methods, compositions and uses for the reduction of hair frizz.

Preferred features of the invention will now be described.

In a preferred embodiment of the present invention there is provided a flowable, optionally anhydrous composition comprising:
a) at least about 2.0%, by weight, of a polysiloxane fluid component selected from one or more of:
i) an amodimethicone component, and
ii) a polysiloxane component comprising a plurality of hindered amine side chains; and
b) a silicone-compatible, volatile liquid carrier component.

Component a) may suitably be an amodimethicone (short for "amino-functionalized dimethicone"—a family of amino functionalized dimethicones and dimethiconols); which genus may include trimethyl silylamodimethicone, or an aminopropyl dimethicone. See the structure below:

wherein X+Y is between about 50 to about 500 and R is a $C_3$ to $C_6$ alkylene group. Such compounds are sold by the Dow Corning Corp. under names such as DOW CORNING X2-8200, DOW CORNING X2-8107, Q2-8220, X2-8123, X2-8124, X2-8120, Softener CSF and X2-8130. In trimethyl silylamodimethicone, R=—$(CH_2)_3$— in the structure immediately above. An aminopropyl dimethicone has the same dimethylsiloxane backbone structure with the pendant group being —$(CH_2)_3$—$NH_2$, and is also available from Dow Corning, Corp. In preferred embodiments, trimethyl silylamodimethicone and/or aminopropyl dimethicone may be used in conjunction, or in place of a polysiloxane component comprising a plurality of hindered amine side chains, as described below, in non-frizz compositions of the invention.

Component a) may therefore suitably comprise a polysiloxane component comprising a plurality of hindered amine side chains.

Such hindered amine side chains have the general formula (Formula 1), pendant from at least one Si atom in the polysiloxane side chain:

Formula 1 wherein $R_1$ is an H, OH, or a $C_1$-$C_5$ hydrocarbon; X is a $C_1$-$C_{10}$ hydrocarbon, a heteroatom, or wherein Z is a heteroatom and d is 0 to about 6. Preferably Z is selected from N, O, S and P. In a preferred embodiment, Z is oxygen and d is about 3.

Preferably the cyclic moiety is a 5-membered ring or a 6-membered ring (e.g. a pyrrolidinyl ring or a piperidinyl ring), particularly, preferably the cyclic moiety is a 6 membered ring.

The cyclic moiety of the side chain may be saturated, partly saturated, or unsaturated.

Preferably, the cyclic moiety is saturated. In preferred examples the side chain has the structure of Formula 2:

Formula 2 wherein $R_1$, $R_2$, $R_3$, $R_4$, $R_5$, $R_6$, $R_7$, $R_8$ and $R_9$ are independently an H, a $C_1$-$C_{10}$ hydrocarbon, an ester, a carboxyl or a halogen, and X is a $C_1$-$C_{10}$ hydrocarbon, a heteroatom, or wherein Z is a heteroatom and d is 0 to about 6.

In some examples X is a $C_1$-$C_5$ hydrocarbon or a heteroatom such as a heteroatom selected from N, O, Si, P, and S, preferably O. In other preferred examples, X is —$(CH_2)_d$—Z—, wherein Z is a heteroatom and d is 0 to about 6.

Preferably, d is from 1 to 4, most preferably 3.

Preferably Z is selected from N, O, S and P most preferably O.

In some preferred examples R1 is H.

In some preferred examples R2, R3, R8 and R9 are each methyl.

In some preferred examples R4, R5, R6 and R7 are each H.

In some preferred examples R1 is H and R2, R3, R8 and R9 are each methyl.

In some preferred examples R1 is H and R2, R3, R8 and R9 are each methyl and X is $(CH_2)_d$—Z—, wherein Z is a heteroatom preferably oxygen and d is 0 to about 6, preferably 1 to 4 preferably 3.

In a preferred example, $R_1$, $R_4$, $R_5$, $R_6$ and $R_7$ are H and $R_2$, $R_3$, $R_8$ and $R_9$ are methyl.

In a preferred example, $R_1$, $R_4$, $R_5$, $R_6$ and $R_7$ are H and $R_2$, $R_3$, $R_8$ and $R_9$ are methyl and X is —$(CH_2)_d$—Z—, wherein Z is a heteroatom preferably oxygen and d is 0 to about 6, preferably 1 to 4 preferably 3.

A preferred polysiloxane component comprising a plurality of hindered amine side chains is an alkoxytetramethyl piperidinyl dimethicone; particularly preferably, a propoxytetramethyl piperidinyl dimethicone component (also called "HNH"). The structure of HNH is shown below, where m and n each is equal to or greater than 1; and in preferred preparations m+n is greater than 2, or greater than about 5, or greater than about 10, or greater than about 20, or greater than about 30, or greater than about 40, or greater than about 50, or greater than about 40, or greater than about 50. Preferably, m+n is less than about 700 or less than about 600, or less than about 500, or between about 50 and about 500.

Such polysiloxane hindered amine compounds, including the preferred alkoxytetramethyl piperidinyl dimethicone component, may be prepared or obtained in a range of molecular weights having a range of viscosities such as from 10 cP to 1 million cP, preferably 100 cP to 100,000 cP; for example, one preparation may have a viscosity of about 200 cP, while another preparation may have a viscosity of about 10,000 cP, while yet another preparation may have a viscosity of about 30,000 cP or 90,000 cP. Blends of HNH preparations having different viscosities may be made to aid in rendering a composition having a desired final viscosity.

Component a) may suitably be a polysiloxane component comprising a plurality of hindered amine side chains comprising one or more of a piperidinyl moiety and/or a pyrrolidinyl moiety. In some examples, component a) comprises a polysiloxane component comprising at least two, or a plurality of, side chains, in which at least one side chain comprises a piperidinyl moiety, and another side chain comprises at least one pyrrolidinyl moiety.

Suitably, in some examples component a) may comprise a combination of one or more polysiloxane hindered amine compounds and one or more amodimethicones.

In some examples component a) may contain a polysiloxane component that comprises both an amodimethicone-type side chain and a plurality of hindered amine side chains as part of a single molecule.

The preferred compositions of the present invention comprises at least 2%, or at least about 2.1%, or at least about 2.2% by weight, or at least about 2.3% by weight, or at least about 2.4% by weight; preferably at least about 2.5% by weight of polysiloxane fluid component a).

Preferably the composition comprises up to about 25%, or up to about 20%, or up to about 18% or up to about 15% by weight of polysiloxane fluid component a). In some embodiments, the composition may comprise at least about 3%, at least about 4% or at least about 5% by weight of polysiloxane fluid component a).

Component b) is a silicone-compatible, volatile liquid carrier component. Component b) may comprise one or more components independently selected from a low molecular weight, volatile siloxy component, a volatile hydrocarbon, and a volatile alcohol.

Component b) provides a volatile liquid carrier for the nonvolatile components of the antifrizz compositions herein, including component a) and other components described herein.

In some embodiments, component b) may comprise a silicone-compatible, volatile liquid carrier component comprising a volatile siloxy component selected from a dimethicone, a dimethiconol, a phenyl methicone, a phenyl methiconol, a phenyl trimethicone, a diphenyl dimethicone, a phenyl dimethicone, and a diphenylsiloxy phenyl trimethicone, a hexamethylsiloxane, a disiloxane, a trisiloxane, cyclotetrasiloxane, cyclopentasiloxane, cyclohexasiloxane, and a mixture of two or more of these components. Typically, the volatile siloxy component will have a viscosity of less than 6 cSt; for example between 0.65 cSt to 3 cSt; such as 1 cSt to 3 cSt. Generally, commercially available preparations of siloxy components within these viscosity ranges contain a distribution of lower and higher viscosity components centered around the stated viscosity of the siloxy component. Siloxy components of 0.65 cSt to 2 cSt are volatile; siloxy component preparations of 3 cSt may be partially volatile.

In some embodiments component b) may comprise a silicone-compatible, volatile liquid carrier component comprising a volatile hydrocarbon, such as isododecane.

In some embodiments component b) may comprise a silicone-compatible, volatile liquid carrier component comprising a volatile alcohol, such as methanol, ethanol, isopropanol or mixtures thereof.

In some examples the silicone-compatible, volatile liquid carrier component b) may comprise a siloxy component and a hydrocarbon component; a siloxy component and an alcohol component; an alcohol component and a hydrocarbon component; or a siloxy component, an alcohol component and a hydrocarbon component.

Thus, in one preferred embodiment, of the present invention there is provided a flowable composition comprising:
a) at least about 2.0%, by weight, of a polysiloxane fluid component selected from one or more of:
i) an amodimethicone component, and
ii) a polysiloxane component comprising a plurality of hindered amine side chains; and b) a silicone-compatible, volatile liquid carrier component selected from: a low molecular weight, volatile siloxy component; a hydrocarbon; and an alcohol.

Preferably such compositions are anhydrous; however, in certain embodiments of the present compositions an aqueous phase may be present.

Preferably the polysiloxane fluid component is present in an amount from at least 2.0% by weight, or at least about 2.5% by weight, or at least about 5% by weight, or at least about 10% by weight to about 15% by weight, or to about 18% by weight, or about 20% by weight.

The silicone-compatible, volatile liquid carrier component is preferably present in an amount from about 22% by weight, to about 97.5% by weight. Optionally, an alkylsiloxysilicate component is present at a concentration from 0% to about 15% by weight.

Optionally, particularly (although not exclusively) for serums, a non-volatile dimethicone and/or dimethiconol component having a viscosity of greater than 60,000 cPs is present in an amount of from about 3% by weight to about 15% by weight. In certain cases the dimethicone or dimethiconol component may be comprised in a co-polymer or cross-polymer.

Optionally, particularly (although not exclusively) for low viscosity anti-frizz serum spritz or spray blends a non-volatile dimethicone and/or dimethiconol component having a viscosity of between about 5 cSt and about 1000 cPs is present in an amount of from about 0.1% by weight to about 20% by weight. In certain cases, the dimethicone or dimethiconol component may be comprised in a co-polymer or cross-polymer.

In another preferred embodiment of the present invention there is provided a flowable composition comprising:
a) at least about 2.0%, by weight, of a polysiloxane fluid component selected from one or more of:
i) an amodimethicone component, and
ii) a polysiloxane component comprising propoxytetramethyl piperidinyl dimethicone component; and
b) a silicone-compatible, volatile liquid carrier component selected from: a dimethicone, a dimethiconol, a phenyl methicone, a phenyl methiconol, a phenyl trimethicone, a diphenyl dimethicone, a phenyl dimethicone, and a diphenylsiloxy phenyl trimethicone, a hexamethylsiloxane, a disiloxane, a trisiloxane, cyclotetrasiloxane, cyclopentasiloxane, cyclohexasiloxane, isododecane, methanol, ethanol, isopropanol or mixtures of two or more of these components.

Preferably such compositions are anhydrous; however, in certain embodiments of the present compositions an aqueous phase may be present.

Preferably the polysiloxane fluid component is present in an amount from at least 2.0% by weight, or at least about 2.5% by weight, or at least about 5% by weight, or at least about 10% by weight to about 15% by weight, or to about 18% by weight, or about 20% by weight.

The silicone-compatible, volatile liquid carrier component is preferably present in an amount from about 22% by weight, to about 97.5% by weight.

Optionally, an alkylsiloxysilicate component is present at a concentration from greater than 0% to about 15% by weight.

Optionally, particularly (although not exclusively) for serums, a non-volatile dimethicone and/or dimethiconol component having a viscosity of greater than 60,000 cPs is present in an amount of from about 3% by weight to about 15% by weight. In certain cases the dimethicone or dimethiconol component may be comprised in a co-polymer or cross-polymer.

Optionally, particularly (although not exclusively) for low viscosity anti-frizz serum spritz or spray blends a non-volatile dimethicone and/or dimethiconol component having a viscosity of between about 5 cSt and about 1000 cPs is present in an amount of from about 0.1% by weight to about 20% by weight. In certain cases, the dimethicone or dimethiconol component may be comprised in a co-polymer or cross-polymer.

If present, the optional alkylsiloxysilicate component may preferably comprise a trimethylsiloxysilicate component, a phenylpropyldimethylsiloxysilicate component or mixtures thereof. Most preferably, the alkylsiloxysilicate component comprises a trimethylsiloxysilicate component.

In preferred examples, the alkylsiloxysilicate component comprises a trimethylsiloxysilicate-based Q resin silicone polymer, known also as MQ resin.

Trimethylsiloxysilicate has the basic structure $(CH_3)_3$—Si—O—Si—$(OH)_3$; the $(CH_3)_3$—Si—O unit is known as an "M" unit, while $SiO_4$ is known as a "Q" unit. An MQ resin is built from M and Q units to form a branched, cage-like oligosiloxane structure that is insoluble in water. Such resins are known to those skilled in the art and are available from Dow Corning Corp. and sold under trade names including DOW CORNING MQ-1600 and DOW CORNING MQ-1640.

Thus in one preferred embodiment, of the present invention there is provided a flowable composition comprising:
 a) at least about 2.0%, by weight, of a polysiloxane fluid component selected from one or more of:
  i) an amodimethicone component, and
  ii) a polysiloxane component comprising a plurality of hindered amine side chains; and
 b) a silicone-compatible, volatile liquid carrier component, and
 c) a trimethylsiloxysilicate-based resin silicone polymer.

Preferably such compositions are anhydrous; however, in certain embodiments of the present compositions an aqueous phase may be present.

Preferably the polysiloxane fluid component is present in an amount from at least 2.0% by weight, or at least about 2.5% by weight, or at least about 5% by weight, or at least about 10% by weight to about 15% by weight, or to about 18% by weight, or about 20% by weight.

The silicone-compatible, volatile liquid carrier component is preferably present in an amount from about 22% by weight, to about 97.5% by weight.

The alkylsiloxysilicate component is preferably present at a concentration from greater than 0% to about 15% by weight.

Particularly (although not exclusively) for serums, a non-volatile dimethicone and/or dimethiconol component having a viscosity of greater than 60,000 cPs may be present in an amount of from about 3% by weight to about 15% by weight. In certain cases the dimethicone or dimethiconol component may be comprised in a co-polymer or cross-polymer.

Particularly (although not exclusively) for low viscosity anti-frizz serum spritz or spray blends a non-volatile dimethicone and/or dimethiconol component having a viscosity of between about 5 cSt and about 1000 cPs may be present in an amount of from about 0.1% by weight to about 20% by weight. In certain cases, the dimethicone or dimethiconol component may be comprised in a co-polymer or cross-polymer.

Thus, in some preferred embodiments the invention provides a flowable composition comprising:
 a) at least 2.0%, by weight, of a polysiloxane fluid component selected from one or more of:
  i) an amodimethicone component, and
  ii) a polysiloxane component comprising a plurality of hindered amine side chains; and
 b) a silicone-compatible, volatile liquid carrier component,
 c) a trimethylsiloxysilicate-based resin silicone polymer, and
 (d) a non volatile component selected from one or more of dimethicone, dimethiconol and phenyl silicone.

The non volatile component d) may comprise a single component, or a mixture of components, and may have a viscosity ranging from about 6 cSt to several million cSt.

The non volatile component d) may comprise one or more of dimethicone, dimethiconol and phenyl silicone components typically referred to as low viscosity (low molecular weight) for example having a viscosity of between 6 to 5000 cSt, intermediate viscosity (intermediate molecular weight) for example having a viscosity between 5000 to 60,000 cSt, high viscosity (high molecular weight) for example having a viscosity >60,000 cSt. The non-volatile component may be present as part of a cross-polymer or co-polymer.

In embodiments where component d) comprises one or more of a high viscosity dimethicone, dimethiconol and phenyl silicone components, the viscosity may be between 60,000 cSt and several million cSt. In some embodiments the viscosity may be between 60,000 cSt and 4 million cSt. In some embodiments, the viscosity may be between 60,000 cSt and 35 million cSt for example when using high molecular weight gums, such as dimethicone gum, or dimethiconol gum.

In embodiments wherein component d) comprises one or more phenyl silicones, the phenyl silicone may include phenyl methicones, phenyl methiconols, phenyl trimethicones diphenyl dimethicones, phenyl dimethicones, and diphenylsiloxy phenyl trimethicones.

In some embodiments, component b) provides a volatile liquid carrier for the non volatile antifrizz components comprising component a), optional component c), and/or optional component d).

Thus, in some embodiments of the invention low molecular weight, volatile dimethicone components such as hexamethylsiloxane, disiloxane and/or trisiloxane may be comprised in the volatile carrier for the non-volatile anti-frizz components (non-volatile polysiloxanes and/or trimethylsiloxysilicate and hindered amine siloxanes such as propoxytetramethyl piperidinyl dimethicone.

"Serum" anti-frizz compositions of the present invention generally contain a combination of a silicone-compatible, non-aqueous volatile carrier and a high molecular weight, high viscosity (e.g., between about 60,000 cSt and about 3 million cSt) dimethicone, dimethiconol or mixture of the two. The final viscosity of the serum generally is in the range of between about 500 cSt to 1000 cSt, or about 2500 cSt, or about 3500 cSt to about 7,500 cSt, or about 7,000 cSt.

The high viscosity polysiloxane component thickens the anti-fizz serum for application control, application aesthetics, and additionally so that it may form a film or coating on the hair fiber. When formulated with a silicone-compatible, non-aqueous volatile carrier the polysiloxane component applies smoothly and provides an excellent hair feel after the carrier evaporates.

When formulated in a composition at higher concentrations, the high viscosity polysiloxane component, particularly when combined with trimethylsiloxysilicate, unexpectedly also aids in increased curl definition and curl memory is also retained under high humidity conditions when 1.5 gram tresses are treated with the composition and evaluated at 80° F. and 80% humidity for 6 hours; (see e.g., Example 10.) While not wishing to be limited by theory, greater curl definition and curl memory is thought to be achieved by removing water from the cortex of the hair shaft during application and/or preventing water from being taken up by the hair and also by reducing the hair fiber-to-hair fiber friction, thus permitting the hair shafts to align against each other and causing an increase in curl definition.

Dimethicones of low and intermediate viscosity, such as a viscosity between about 6 cSt to 60,000 cSt can be used as instead of, or in combination with the high molecular weight siloxanes (e.g. dimethicone or dimethiconol) to keep the viscosity of the anti-frizz serum, spritz or spray within the desired viscosity for their intended use; serums are commonly used after shampooing and/or conditioning as a leave-in agent, while sprays and "spritzes" are generally used as a touchup during the day.

Additionally, phenyl silicones such as phenyl methicones, phenyl methiconols, phenyl trimethicones, diphenyl dimethicones, phenyl dimethicones, and diphenylsiloxy phenyl trimethicones and the like can used in place of, or in combination with, either high, intermediate, or low viscosity dimethicone, dimethiconols, volatile hydrocarbons and/or alcohols in, for example, low viscosity applications. Like the siloxanes described above, these materials can improve the ease of application ("spreadability") of the composition on the hair and improve hair shine.

In some embodiments, the composition of the present invention may optionally contain one or more additional ingredients. For example, the additional ingredient may comprise one or more components selected from the group consisting of:
- a colorant component (such as a cosmetically approved silicone-soluble dye),
- a hair shine ingredient (such as one or more ingredient selected from phenyltrimethicone, diphenylsiloxy phenyl trimethicone, diphenyl dimethicone, caprylic/capric triglycerides, mineral or natural oils, and alkyl benzoates),
- a sunscreen ingredient (such as titanium oxide and zinc oxide),
- an aesthetic modifier component (e.g., thickener components, preservative components, fragrance components, pH adjustment components, plasticizer components, appearance modifiers and/or anti-oxidant components). Such agents may include one or more of the following medium to high molecular weight silicone components; dimethicone crosspolymer, dimethicone/vinyl dimethicone crosspolymer, dimethicone/phenyl vinyl dimethicone crosspolymer, vinyl dimethicone/lauryl dimethicone crosspolymer, lauryl polydimethylsiloxyethyl dimethicone/bis-vinyl dimethicone crosspolymer, alkyl silicones, stearoxytrimethylsilane, ethylene-dimethicone copolymer, polyethylsiloxanes, alkyl silicones including caprylyl methicone, lauryl methicone and stearoxymethicone,
- an essential oil component,
- a botanical component,
- a scent component,
- a nucleic acid component,
- a specialty extract component, and
- a vitamin.

In some embodiments, the methods and compositions disclosed herein may be used on hair that has not been artificially dyed or pigmented.

In other embodiments, the methods and compositions disclosed may be used on hair that has been artificially dyed or pigmented, for example to retain hair color.

In some examples the compositions may comprise a polysiloxane component in a water-in-oil or oil-in-water emulsion with an aqueous solvent while, in other, preferred examples, the compositions of the invention are anhydrous or substantially anhydrous.

In some presently less preferred examples the compositions of the present invention may comprise a polysiloxane component in combination with a detersive component (for example, as a component of a "conditioning shampoo" formulation); while in other, more preferred, examples the compositions of the present invention are not formulated in a shampoo formulation or used to clean hair or skin, and even more preferably, lack a detersive component. By a "detersive component" is meant a composition comprising a surfactant concentration is effective to clean dirt or oil from skin or hair when used as an ordinary soap or shampoo.

In some examples, the compositions of the present invention may cause a reduction in hair frizz at 80° F. and 80% humidity relative to untreated otherwise identical frizzy hair under the same temperature and humidity conditions.

A preferred method for measuring the reduction in hair frizz is the High Humidity Frizz Control Test Method defined in the examples. Reduction in hair fizz is suitably measured relative to untreated frizzy hair under the same temperature and humidity conditions, preferably at a temperature of 80° F. and 80% humidity.

In some embodiments, the compositions of the present invention may cause at least a 70% reduction in hair frizz at 80° F. and 80% humidity relative to untreated otherwise identical frizzy hair under the same temperature and humidity conditions.

In some embodiments, the compositions of the present invention may cause at least a 75% reduction in hair frizz at 80° F. and 80% humidity relative to untreated otherwise identical frizzy hair under the same temperature and humidity conditions.

In some embodiments, the compositions of the present invention may cause at least an 80% reduction in hair frizz at 80° F. and 80% humidity relative to untreated otherwise identical frizzy hair under the same temperature and humidity conditions.

In some embodiments, the compositions of the present invention may cause at least an 85% reduction in hair fizz at 80° F. and 80% humidity relative to untreated otherwise identical frizzy hair under the same temperature and humidity conditions.

In some embodiments, the compositions of the present invention may cause at least a 90% reduction in hair frizz at 80° F. and 80% humidity relative to untreated otherwise identical frizzy hair under the same temperature and humidity conditions.

In some embodiments, the compositions of the present invention may cause at least a 95% reduction in hair frizz at 80° F. and 80% humidity relative to untreated otherwise identical frizzy hair under the same temperature and humidity conditions.

In some embodiments, the compositions of the present invention may cause between about 75% and 95% reduction in hair frizz at 80° F. and 80% humidity relative to untreated otherwise identical frizzy hair under the same temperature and humidity conditions.

In some embodiments, the compositions of the present invention may cause between about 80% and 90% reduction in hair frizz at 80° F. and 80% humidity relative to untreated otherwise identical frizzy hair under the same temperature and humidity conditions.

In some embodiments, the compositions of the present invention may cause between about 85% and 90% reduction in hair frizz at 80° F. and 80% humidity relative to untreated otherwise identical frizzy hair under the same temperature and humidity conditions.

In the some embodiments of the present invention there is provided a method of reducing or preventing hair frizz, comprising the steps:
I) applying to hair a composition as described herein; and
II) distributing said composition along a plurality of hair shafts.

In another embodiment of the present invention there is provided the use of a composition as described herein to reduce hair frizz.

In a preferred embodiment, the present invention provides a method of reducing or preventing hair frizz, comprising the steps:
I) applying to hair a composition as described herein; and
II) distributing said composition along a plurality of hair shafts;
wherein the reduction in hair frizz is measured relative to untreated frizzy hair under the same temperature and humidity conditions In a preferred embodiment the present invention provides the use of a composition as described herein to reduce hair frizz; wherein the reduction in hair fizz is measured relative to untreated frizzy hair under the same temperature and humidity conditions.

The further examples provided below are intended to illustrate various embodiments of the invention, and are not intended to limit the scope of any claim. Hence it is the claims alone that define the scope of the invention, including any equivalents thereof.

In one example the invention is directed to an anhydrous blend comprising: a carrier containing a anhydrous alcohol, volatile silicone or volatile hydrocarbon; a high molecular weight (HMW) dimethicone having a viscosity of between about 60,000 cSt (centistokes) and about 4 million cSt; an alkylsiloxysilicate such as trimethylsiloxysilicate; a propoxytetramethyl piperidinyl dimethicone component, preferably having a viscosity of from about 10,000 cSt to about 100,000 cSt.

Thus, in one example, the invention is directed to an anhydrous composition that provides greater than 80% reduction of hair frizz caused by high humidity, said composition comprising a serum blend containing an anti-fizz component selected from the group consisting of: greater than 2%, or greater than about 2.1%, or greater than about 2.2%, or greater than about 2.3%, or greater than about 2.4%, or greater than about 2.5%, or greater than about 4%, or greater than about 5%, or greater than about 10%, or greater than about 15%, by weight, of a propoxytetramethyl piperidinyl dimethicone component.

In another example the invention is directed to an anhydrous serum composition that provides greater than about 80% reduction of hair frizz caused by high humidity, the composition comprising from 2.0%, or about 2.5% to about 20%, by weight, of propoxytetramethyl piperidinyl dimethicone; from about 3% to about 15%, by weight, of at least one dimethicone component, and/or dimethiconol component, having a viscosity of greater than about 60,000 cSt; a further component having from 0% to about 15%, by weight, of a compound selected from the group consisting of trimethylsiloxysilicate, phenylpropyldimethylsiloxysilicate and mixtures thereof; and from about 50% to about 94.5%, by weight, of a silicone-compatible, non-aqueous volatile carrier. Preferably, the silicone-compatible, non-aqueous volatile carrier is selected from the group consisting of cyclotetrasiloxane, cyclopentasiloxane, cyclohexasiloxane, hexamethyldisiloxane, trisiloxane, trimethicone, a dimethicone with a viscosity between about 1.5 cSt and about 4 cSt, isododecane, anhydrous alcohol, a substituted or unsubstituted $C_1$ to $C_8$ alkyl chain siloxane, and mixtures of two or more of these. Preferably the substituted or unsubstituted $C_1$ to $C_8$ alkyl chain siloxane is selected from the group consisting of diethylsiloxane, caprylyl methicone, and mixtures thereof.

In another example the invention is directed to a low viscosity serum, spritz or spray composition that provides greater than 80% reduction of high humidity frizz, and has a final viscosity of less than about 800 cps. The composition comprises from about 2.0% to about 20%, by weight, of propoxytetramethyl piperidinyl dimethicone; about 0% to about 20%, by weight, of at least one dimethicone component and/or dimethiconol component with a viscosity of between about 5 cSt and about 1000 cSt; from about 0% to about 20%, by weight, of a compound selected from the group consisting of trimethylsiloxysilicate, phenylpropyldimethylsiloxysilicate and mixtures thereof; and from about 40% to about 97.5%, by weight, of a silicone-compatible, non-aqueous volatile carrier. Preferably, the silicone-compatible, non-aqueous volatile carrier is selected from the group consisting of cyclotetrasiloxane, cyclopentasiloxane, cyclohexasiloxane, hexamethyldisiloxane, trisiloxane, trimethicone, isododecane, a dimethicone with a viscosity between about 1.5 cSt. and about 4 cSt, a substituted or unsubstituted $C_1$ to $C_8$ alkyl chain siloxane and mixtures of two or more of these. Preferably the substituted or unsubstituted $C_1$ to $C_8$ alkyl chain siloxane is selected from the group consisting of diethylsiloxane, caprylyl methicone and mixtures thereof.

In another example, the invention is drawn to a low viscosity spritz or spray blend that provides greater than 80% reduction of high humidity frizz and has a final viscosity of less than about 800 cps. The composition comprises from 2.0%, or about 2.5% to about 20%, by weight, of propoxytetramethyl piperidinyl dimethicone; from 0% to about 15% by weight of at least one non-volatile dimethicone component and/or dimethiconol component, having a viscosity of greater than about 5 cSt and less than 10 cSt; from about 0.1% to about 20%, by weight, of a compound selected from the group consisting of trimethylsiloxysilicate, phenylpropyldimethylsiloxysilicate and mixtures thereof; and from about 45% to about 97.4%, by weight, of a silicone-compatible, non-aqueous volatile carrier. Preferably the silicone-compatible, non-aqueous volatile carrier is selected from the group consisting of cyclotetrasiloxane; cyclopentasiloxane; cyclohexasiloxane; hexamethyldisiloxane; trisiloxane or trimethicone; dimethicone with viscosities ranging from about 1.5 cSt. to about 4 cSt; anhydrous ethanol; isododecane and blends of two or more of these components. Preferably, the substituted or unsubstituted $C_1$ to $C_8$ alkyl chain siloxane is selected from the group consisting of diethylsiloxane, caprylyl methicone and blends thereof.

In another example, the invention is directed to a composition comprising a low viscosity spritz or spray blend that provides greater than 80% reduction of high humidity frizz, and has a viscosity of less than about 500 cps. The composition comprises from about 2.5% to about 20%, by weight, of propoxytetramethyl piperidinyl dimethicone; from 0% to about 20% of at least one non-volatile dimethicone component and/or dimethiconol component having a viscosity of greater than about 5 cSt and less than about 10 cSt; and from about 60% to about 97.4%, by weight, of a silicone-compatible, non-aqueous volatile carrier. Preferably the silicone-compatible, non-aqueous volatile carrier is selected from the group consisting of cyclotetrasiloxane; cyclopentasiloxane; cyclohexasiloxane; hexamethyldisiloxane; trisiloxane or trimethicone; dimethicone with viscosities ranging from about 1.5 cSt. to about 4 cSt; anhydrous ethanol; isododecane and blends of two or more of these components. Preferably, the substituted or unsubstituted $C_1$ to $C_8$ alkyl chain siloxane is selected from the group consisting of diethylsiloxane, caprylyl methicone and blends thereof.

In another example, the invention is drawn to a composition comprising a serum blend that provides greater than about 80% reduction of high humidity frizz. The composition comprises from 2.0%, or about 2.5% to about 20%, by weight, of propoxytetramethyl piperidinyl dimethicone; from about 3% to about 15% of at least one dimethicone component and/or dimethiconol component having a viscosity of greater than about 60,000 cSt from 0.1% to about 15%, by weight, of a phenyl modified silicone; from 0% to about 15%, by weight, of a compound selected from the group consisting of trimethylsiloxysilicate, phenylpropyldimethylsiloxysilicate, and mixtures thereof; and from about 35% to about 94.4%, by weight, of a silicone-compatible, non-aqueous volatile carrier. Preferably, the silicone-compatible, non-aqueous volatile carrier is selected from the group consisting of cyclotetrasiloxane, cyclopentasiloxane, cyclohexasiloxane, hexamethyldisiloxane, trisiloxane or trimethicone, dimethicone with viscosities of from about 1.5 cSt to about 4 cSt; a diethylsiloxane, isododecane, a substituted or unsubstituted $C_1$ to $C_8$ alkyl chain siloxane, and blends of two or more of these components. Preferably the $C_1$ to $C_8$ alkyl chain siloxane comprises caprylyl methicone. Preferably the phenyl dimethicone comprises a compound selected from the group consisting of phenyltrimethicone, diphenyl dimethicone, diphenylsiloxy phenyl trimethicone and phenyl dimethicone.

In another example, the invention is drawn to a composition comprising a low viscosity serum, spritz or spray composition that provides greater than 80% reduction of high humidity frizz and has a viscosity of less than about 800 cps. The composition comprises from 2.0%, or about 2.5% to about 20%, by weight, of propoxytetramethyl piperidinyl dimethicone; from about 0% to about 8%, by weight, of a first dimethicone component, and/or dimethiconol component with a viscosity of greater than 60,000 cSt; from 0.1% to about 15%, by weight, of a second non-volatile dimethicone component and/or dimethiconol component, having a viscosity of about 5 cSt to about 1000 cSt; from 0.1% to about 15%, by weight, of a phenyl modified silicone; from 0% to about 20%, by weight, of a compound selected from the group consisting of trimethylsiloxysilicate, phenylpropyldimethylsiloxysilicate and mixtures thereof; and from about 22% to about 97.3%, by weight, of a silicone-compatible, non-aqueous volatile carrier. Preferably the phenyl-modified silicone is selected from the group consisting of phenyltrimethicone, diphenyl dimethicone, diphenylsiloxy phenyl trimethicone, phenyl dimethicone and mixtures thereof. Preferably the silicone-compatible, non-aqueous volatile carrier is selected from the group consisting of cyclotetrasiloxane, cyclopentasiloxane, cyclohexasiloxane, hexamethyldisiloxane, trisiloxane, trimethicone, isododecane, a dimethicone with viscosities ranging from about 1.5 cSt to about 4 cSt, a diethylsiloxane, a substituted or unsubstituted $C_1$ to $C_8$ alkyl chain siloxane, and mixtures of two or more of these. Preferably the $C_1$ to $C_8$ alkyl chain siloxane comprises caprylyl methicone.

In another example, the invention is drawn to a composition comprising a low viscosity spritz or spray composition that provides greater than 80% reduction of high humidity fizz and has a viscosity of less than about 800 cps. The composition comprises from 2.0%, or about 2.5% to about 15%, by weight, of propoxytetramethyl piperidinyl dimethicone; from 0% to about 15%, by weight, of a non-volatile dimethicone component and/or dimethiconol component, having a viscosity of about 5 cSt to about 10 cSt; from 0.1% to about 15%, by weight, of a phenyl modified silicone; from about 0.1% to about 20%, by weight, of a compound selected from the group consisting of trimethylsiloxysilicate, phenylpropyldimethylsiloxysilicate and mixtures thereof; and from about 35% to about 97.3%, by weight, of a silicone-compatible, non-aqueous volatile carrier. Preferably the phenyl-modified silicone is selected from the group consisting of phenyltrimethicone, diphenyl dimethicone, diphenylsiloxy phenyl trimethicone, phenyl dimethicone and mixtures thereof. Preferably the silicone-compatible, non-aqueous volatile carrier is selected from the group consisting of cyclotetrasiloxane, cyclopentasiloxane, cyclohexasiloxane, hexamethyldisiloxane, trisiloxane, trimethicone, isododecane, a dimethicone with viscosities ranging from about 1.5 cSt to about 4 cSt, a diethylsiloxane, an anhydrous ethanol, a substituted or unsubstituted $C_1$ to $C_8$ alkyl chain siloxane, and mixtures of two or more of these components. Preferably the $C_1$ to $C_8$ alkyl chain siloxane comprises caprylyl methicone.

In another example, the invention is drawn to a composition comprising a high shine serum spritz or spray blend composition that provides greater than 80% reduction of high humidity fizz and has a viscosity of less than about 500 cps. The composition comprises from 2.0%, or about 2.5% to about 15%, by weight, of propoxytetramethyl piperidinyl dimethicone; from about 0.1% to about 15%, by weight, of a phenyl modified silicone; and from about 65% to about 97.4% by weight, of a silicone-compatible, non-aqueous volatile carrier. Preferably the phenyl-modified silicone is selected from the group consisting of a phenyl methicone, a phenyl methiconol, a phenyl trimethicone, a diphenyl dimethicone, a diphenylsiloxy phenyl trimethicone, a phenyl dimethicone and mixtures of two or more of these components. Preferably the silicone-compatible, non-aqueous volatile carrier is selected from the group consisting of cyclotetrasiloxane, cyclopentasiloxane, cyclohexasiloxane, hexamethyldisiloxane, trisiloxane, trimethicone, isododecane, a dimethicone with viscosities ranging from about 1.5 cSt to about 4 cSt, a diethylsiloxane, an anhydrous ethanol, a substituted or unsubstituted $C_1$ to $C_8$ alkyl chain siloxane, and mixtures of two or more of these. Preferably the $C_1$ to $C_8$ alkyl chain siloxane comprises caprylyl methicone.

The use of propoxytetramethyl piperidinyl dimethicone (also called "HNH") at concentrations at or above 2.0%, or about 2.5%, by weight, and the use of one or more silicone-compatible, non-aqueous volatile carriers are common ingredients in most of the examples listed above. In one major example of the invention, the inventors have surprisingly discovered that the combination of these two ingredients, particularly (but not solely) when combined with a high or medium molecular weight dimethicone or other methyl or hydroxyl end-blocked gum of about 60,000 cSt to about 35 million cSt, strongly contribute to the ability of the compositions to reduce humidity-induced hair frizz by 80% or more.

EXAMPLES

High Humidity Frizz Control Test Method

Approximately 1.5 grams (weight of the hair) curly hair (Brazilian) [International Hair Importers; 8729 Myrtle Ave; Glendale New York 11385] is pre-washed 2× with a 10% by weight SLES-2 (sodium lauryl ethoxy sulfate having an average of 2 moles of ethylene oxide) solution in water. The wet hair tresses are hung overnight in a temperature/humidity chamber set at 80° F./80% relative humidity (RH).

Tresses are then removed from the chamber, coded and photos are taken with a high-resolution camera. Pictures are used as a baseline for initial frizz value analysis using image analysis software permitting numerical analysis of the optical properties of curly, frizzy, and African hair types, and measurement of hair fiber alignment with 2-D Fourier transform. [Image-Pro Plus® version 7.0; Media Cybernetics, Inc., 4340 East-West Highway, Suite 400, Bethesda, MD 20814].

After the pictures are taken, tresses are pre-wet under running water for 10 seconds and towel dried. 50 µl of each test formulation is hand-applied to the tress from the root end down. The test formulation is distributed as evenly as possible along the hair.

After the application of a test formulation, the tresses are hung in the humidity chamber set at 80° F. (27° C.)/80% RH for 6 hours.

Post-treatment photos of the hair are taken. Pre- and post-treatment photos are used in conjunction with the Image Pro Plus® software. Photos are used to compare these images and analyze the reduction in frizz values in the treated tresses (frizz protection) vs. the frizz values of the untreated, humidified tresses to obtain numerical values for percent frizz reduction.

Example 1

Formulations of some commercially available anti-frizz products were purchased and evaluated for frizz control and are represented in Table 1, below.

TABLE 1

|  | Formulation A Serum | Formulation B Serum | Formulation C Serum |
| --- | --- | --- | --- |
|  | Cyclopentasiloxane | Cyclopentasiloxane | Cyclopentasiloxane |
|  | Dimethicone | Dimethiconol | Dimethiconol |
|  | Capric and Caprylic Triglycerides | Mineral oil | Mineral oil |
|  | Dimethiconol |  |  |
|  | Fragrance and other inactive ingredients* | Fragrance and other inactive ingredients* | Fragrance and other inactive ingredients* |
| % Frizz Reduction | 75% | 70% | 68% |
| % Solids | 35.47% | 14.46% | 15.54% |

|  | Formulation D | Formulation E |
| --- | --- | --- |
|  | Anhydrous Spray | Water Based Emulsion Spray |
|  | Alcohol | Water |
|  | Cyclopentasiloxane | Cetearyl Alcohol |
|  | Bis-phenylpropyl Dimethicone | Behentrimonium Chloride |
|  | Dimethicone | Propylene Glycol |
|  | C12-15 Alkyl Benzoate | Cyclomethicone |
|  | Fragrance and other inactive ingredients | Fragrance and other inactive ingredients |
| % Frizz Reduction | 30% | 17% |
| % Solids | 6.27% | 5.30% |

As shown in Table 1, none of Formulations A-E provides fizz reduction, relative to untreated tresses, at a level greater than 75%. Formulation A contains capric/caprylic triglycerides, a purified, fractionated derivative of coconut oil. Formulations B and C include mineral oil. As discussed previously, oils have both practical and aesthetic disadvantages. They tend to stain fabrics (such as clothing, sheets, pillowcases), have a heavy feel and may leave hair with an undesired slicked, "wet" appearance.

Example 2

Sample anti-frizz serum formulations were made as shown in Table 2, below. Ingredients are given in weight percent; unless otherwise indicated, all concentration percentages given in this patent application are weight percentages. The ingredients are simply combined and then fully mixed to form a solution.

TABLE 2

| Ingredients | Formulations | | | | | |
|---|---|---|---|---|---|---|
|  | 1 | 2 | 3 | 4 | 5 | 6 |
| Dimethicone 2 cSt | 70.00 | 80.00 | 70.00 | 75.0 | 75.0 | 80.0 |
| Propoxytetramethyl Piperidinyl Dimethicone (HNH) Viscosity ~30,000 | 10.00 |  |  | 10.0 |  | 10.0 |
| Propoxytetramethyl Piperidinyl Dimethicone (HNH) Viscosity ~10,000 |  | 10.00 | 10.00 |  | 10.0 |  |
| Dimethicone gum | 10.00 | 10.00 | 10.00 | 10.0 | 10.0 | 10.0 |
| Trimethylsiloxysilicate | 10.00 |  | 10.00 | 5.0 | 5.0 |  |
| Frizz reduction | 94% | 95% | 89% | 85% | 90% | 90% |
| Brookfield Viscosity (cps) | 2760 | 1640 | 1040 | 600 | 2030 | 1500 |

Formulations 1-6 are drawn to typical viscosities of "leave on" anti-frizz serum compositions. The formulations contain: 10% of propoxytetramethyl piperidinyl dimethicone (HNH) at one of two average viscosities (about 30,000 cP or about 10,000 cP); at least 70% of a volatile carrier comprising a low molecular weight dimethicone having a viscosity of 2 cSt; and 10% of a higher molecular weight, non-volatile dimethicone gum with a typical viscosity range of about 19,000,000 cP to about 35,000,000 cP. Additionally, Formulations 1 and 3-5 contain either 10% or 5% of trimethylsiloxysilicate MQ resin.

Hair treated with each of Formulations 1 through 6 show at least 80% frizz reduction relative to untreated tresses; this degree of frizz reduction is significantly greater than the frizz reduction provided by prior formulations 1A-1C. The percent frizz reduction for hair treated with Formulations 1-6 is 94%, 95%, 89%, 85%, 90%, and 90%, respectively. Among these samples, the formulation yielding the highest degree of frizz reduction (95%) is Formulation 2, which contains only the lower viscosity (10,000 cP) HNH component, the highest percentage (80%) of the dimethicone carrier, and lacks trimethylsiloxysilicate.

Example 3

Table 3 shows an additional set of sample serum formulations. Each formulation is made by combining ingredients together to form an anhydrous solution.

TABLE 3

| Ingredients | Formulations | | | |
|---|---|---|---|---|
|  | 7 | 8 | 9 | 10 |
| Dimethicone 1.5 cSt | 75.0 | 75.0 | 80.0 | 70.00 |
| Propoxytetramethyl Piperidinyl Dimethicone (HNH) Viscosity ~30,000 | 10.0 |  | 10.0 | 10.00 |
| Propoxytetramethyl Piperidinyl Dimethicone (HNH) Viscosity ~10,000 |  | 10.0 |  |  |
| DM-gum | 10.0 | 10.0 | 10.0 | 10.00 |
| Trimethylsiloxysilicate | 5.0 | 5.0 |  | 10.00 |
| Frizz reduction | 85% | 90% | 90% | 86% |
| Brookfield Viscosity cps | 720 | 845 | 1200 | 920 |

Formulations 7-10 are another set of relatively low viscosity anti-frizz preparations. These formulations contain: 10% of HNH at one of two average viscosities (about 30,000 cP or about 10,000 cP); at least 70% of a volatile carrier comprising a low molecular weight dimethicone having a viscosity of 1.5 cSt; and 10% of a higher molecular weight, non-volatile dimethicone gum with a typical viscosity range of about 19,000,000 cP to about 35,000,000 cP. Additionally, Formulations 7, 8 and 10 contain either 10% or 5% of trimethylsiloxysilicate MQ resin.

Hair treated with each of Formulations 7 through 10 show at least 85% frizz reduction relative to untreated tresses. The percent frizz reduction for hair treated with Formulations G-J is 85%, 90%, 90%, and 86%, respectively.

Example 4

Table 4 shows an additional set of sample serum formulations. Each formulation is made by combining and mixing ingredients together to form an anhydrous solution.

TABLE 4

| Ingredients | Formulations | | | | | |
|---|---|---|---|---|---|---|
| | 11 | 12 | 13 | 14 | 15 | 16 |
| Cyclopentasiloxane | 74.50 | 60.00 | 80.16 | 66.67 | 65.78 | 77.50 |
| Propoxytetramethyl Piperidinyl Dimethicone (HNH) Viscosity ~30,000 cP | 2.50 | 14.17 | 19.16 | 20.00 | 5.78 | 2.50 |
| Dimethicone gum | 11.50 | 12.50 | 4.8 | 6.67 | 13.59 | 20.00 |
| Trimethylsiloxysilicate | 11.50 | 13.33 | 4.8 | 6.67 | 14.84 | |
| Frizz control | 83% | 89% | 84% | 91% | 92% | 86% |
| Brookfield Viscosity cps | 5200 | 37,000 | 2000 | 6070 | 16,950 | 29,000 |

Formulations 11-16 are a set of low to medium viscosity anti-frizz preparations. These formulations contain: various concentrations of HNH at an average viscosity of about 30,000 cps; from about 59% to about 77% of a volatile carrier comprising a cyclopentasiloxane; and from about 6.5% to 20% of a higher molecular weight, non-volatile dimethicone with a typical viscosity range of about 19,000,000 cP to about 35,000,000 cP. Additionally, Formulations 11-16 contain from about 6.7% to about 14.8% of trimethylsiloxysilicate MQ resin.

Hair treated with each of Formulations 11 through 16 show at least 83% frizz reduction relative to untreated tresses, with Formulation 11 yielding an 83% reduction in frizz and Formulation 15 yielding a 92% reduction in frizz. Blends of volatile carriers such as cyclomethicones; volatile dimethicones having a viscosity of from about 0.65 to about 4 cSt;) and volatile hydrocarbon and/or alcohol-based carriers such as methanol or isododecane are anticipated to have similar frizz reduction effects.

Example 5

Another set of low viscosity serum non-frizz formulations are established as follows, by combining the components and then mixing until homogeneous:

TABLE 5

| Ingredients | Formulations | | |
|---|---|---|---|
| | 17 | 18 | 19 |
| Cyclopentasiloxane | 72.50 | | |
| Dimethicone 2 cSt | | 87.50 | 85.00 |
| Propoxytetramethyl Piperidinyl Dimethicone (HNH) Viscosity ~30,000 cP | 14.17 | 2.50 | 5.00 |

TABLE 5-continued

| Ingredients | Formulations | | |
|---|---|---|---|
| | 17 | 18 | 19 |
| Piperidinyl Dimethicone (HNH) Viscosity ~30,000 cP | | | |
| Dimethicone gum | | 5.00 | 5.00 |
| Trimethylsiloxysilicate | 13.33 | 5.00 | 5.00 |
| Frizz reduction | 92% | 90% | 82% |
| Brookfield Viscosity cP | 272 | 190 | 210 |

In the examples shown in Table 5, Formulations 17 through 19 are made using the following components: from about 72.5% to about 87.5% of either cyclopentasiloxane or low molecular weight dimethicone (viscosity 2 cSt) as a volatile, silicone compatible carrier; from 2.5% to about 14.17% of HNH having a viscosity of about 30,000 cP; from 2.5 to about 5.8% dimethicone gum; and from about 4.8% to 20% of trimethylsiloxysilicate MQ resin.

When tresses are individually treated with the formulations of Table 5, they show a percent frizz reduction, relative to untreated tresses, of greater than 80%; from an 82% reduction for Formulation 32 to a 90% reduction for Formulation 19.

Example 6

Table 6 shows sprayable Formulations 20-25, made using the following components and made by combining the components and then mixing until homogeneous:

TABLE 6

| Ingredients | Formulations | | | | | |
|---|---|---|---|---|---|---|
| | 20 | 21 | 22 | 23 | 24 | 25 |
| Cyclopentasiloxane | 97.50 | 88.75 | | | | |
| Dimethicone 2 cSt | | | 89.50 | 89.50 | 89.50 | 80.00 |
| Propoxytetramethyl Piperidinyl Dimethicone (HNH) Viscosity ~30,000 cP | 2.50 | 11.25 | 10.00 | 10.00 | | 10.00 |
| Propoxytetramethyl Piperidinyl Dimethicone (HNH) Viscosity ~10,000 cP | | | | | 10.00 | |
| Trimethylsiloxysilicate | | | 0.50 | 0.50 | 0.50 | 10.00 |
| Frizz Reduction | 86% | 93% | 82% | 82% | 80% | 80% |
| Viscosity cP | ~40 | ~80 | ~80 | ~60 | ~40 | ~70 |

Formulations 20-25 are made using the following components: from about 80% to about 97.5% of either cyclopentasiloxane or low molecular weight dimethicone (viscosity 2 cSt) as a volatile, silicone compatible carrier; from about 2.5% to about 11.25% of HNH having a viscosity of about 30,000 cP or about 10% of NHN having a viscosity of about 10,000 cP; and from 0 to about 10% of trimethylsiloxysilicate MQ resin.

When tresses are individually treated with any of the formulations of Table 6, they show a percent frizz reduction, relative to untreated tresses, of about 80% or greater; from about 80% reduction for Formulations 24 and 25 to about 93% reduction for Formulation 21.

Example 7

Table 7 shows anti-frizz serum-type Formulations 26-30, each of which is made by combining the indicated components and then mixing until homogeneous.

TABLE 7

| | Formulations | | | | |
|---|---|---|---|---|---|
| Ingredients | 26 | 27 | 28 | 29 | 30 |
| Isododecane | 75.00 | | 37.58 | | |
| Trisiloxane | | 69.00 | 37.58 | 27.00 | 45.00 |
| Dimethicone 2 cSt | | | | 35.00 | 30.00 |
| Dimethicone 6 cSt | | | 2.00 | | |
| Propoxytetramethyl Piperidinyl Dimethicone (HNH) | 10.00 | 14.00 | 8.00 | 12.00 | 5.00 |
| Dimethicone gum | 15.00 | 12.00 | 10.00 | 11.00 | 10.00 |
| Trimethylsiloxysilicate | 10.00 | 5.00 | 4.84 | 15.00 | 10.00 |

Each of Formulations 26-30, indicated above, contain propoxytetramethyl piperidinyl dimethicone (HNH), dimethicone gum, and trimethylsiloxysilicate MQ resin. The volatile carrier component in Formulations 26 and 28 comprises the hydrocarbon isododecane; in Formulations 27-30, the volatile carrier component comprises trisiloxane. Formulation 28 has a volatile carrier component comprising a mixture of low molecular weight dimethicone (viscosity 6 cSt) and trisiloxane. Formulations 29 and 30 have a volatile carrier component comprising a mixture of a low molecular weight dimethicone (viscosity 2 cSt) and trisiloxane.

In each case when tresses are individually treated with any of the formulations of Table 7, they show a percent frizz reduction, relative to untreated tresses, of about 80% or greater.

Example 8

Table 8 shows a set of serums, spritz and/or spray formulations.

TABLE 8

| | Formulations | | | |
|---|---|---|---|---|
| Ingredients | 31 | 32 | 33 | 34 |
| Cyclomethicone | | 60.00 | | |
| Dimethicone 2 cSt | 40.00 | | 41.50 | |
| Isododecane | 40.00 | | 30.00 | 32.00 |
| Anhydrous Ethanol | | 20.00 | | 20.00 |
| Dimethicone 5 cSt | 10.00 | | | 15.00 |
| Dimethicone 6 cSt | | 10.00 | 15.00 | |
| Propoxytetramethyl Piperidinyl Dimethicone (HNH) | 5.00 | 10.00 | 3.00 | 18.00 |
| Dimethiconol gum | 5.00 | | 3.00 | |
| Trimethylsiloxysilica | 5.00 | 5.00 | 15.00 | 15.00 |

Each of Formulations 31-34, indicated above, contain propoxytetramethyl piperidinyl dimethicone (HNH) and trimethylsiloxysilicate MQ resin.

The volatile carrier component in Formulation 32 comprises a mixture of cyclomethicone and anhydrous ethanol; Formulation 32 has no dimethicone gum, but contains dimethicone with a viscosity of 6 cSt. In Formulation 34, the volatile carrier component comprises a mixture of anhydrous ethanol and isododecane, has no dimethicone gum, but contains dimethicone with a viscosity of 5 cSt. The viscosity of the propoxytetramethyl piperidinyl dimethicone (or of a mixture of HNH species having different viscosities) may have any concentration within the range between about 250 cP and 30,000 cP, or within the range about 10,000 cP.

Formulations 31 and 33 have a volatile carrier component comprising a mixture of isododecane and low molecular weight dimethicone (2 cSt), and both contain dimethicone gum. Formulation 31 also comprises dimethicone with a viscosity of 5 cSt, while Formulation 33 has dimethicone at a viscosity of 6 cSt.

In each case when tresses are individually treated with any of the formulations of Table 8, they show a percent frizz reduction, relative to untreated tresses, of about 80% or greater.

Example 9

Table 9 includes anti-frizz non-aerosol spray Formulations 35-40.

TABLE 9

| | Formulations | | | | | |
|---|---|---|---|---|---|---|
| Ingredients | 35 | 36 | 37 | 38 | 39 | 40 |
| Cyclomethicone | | 67.00 | | | 75.00 | 70.00 |
| Dimethicone 2 cSt | 28.50 | | 87.50 | 27.00 | | |
| Isododecane | 50.00 | | | 50.00 | | |
| Anhydrous Ethanol | | 20.00 | | | 15.00 | 15.00 |
| Dimethicone 5 cSt | 10.00 | | 8.00 | | | |
| Dimethicone 6 cSt | | 7.00 | | 8.00 | | 5.00 |
| Propoxytetramethyl Piperidinyl Dimethicone (HNH) | 11.50 | 6.00 | 4.50 | 15.00 | 10.00 | 10.00 |

Formulations 35-40 lack dimethicone gum and trimethylsiloxysilicate, but all contain propoxytetramethyl piperidinyl dimethicone and comprise high percentages of the volatile carrier component, which may be cyclomethicone, low molecular weight dimethicone, isododecane, anhydrous ethanol, or a mixture thereof.

Each of Formulations 35-40 is expected to show a percent frizz reduction, relative to untreated tresses, of about 80% or greater.

Example 10

Figure 1:
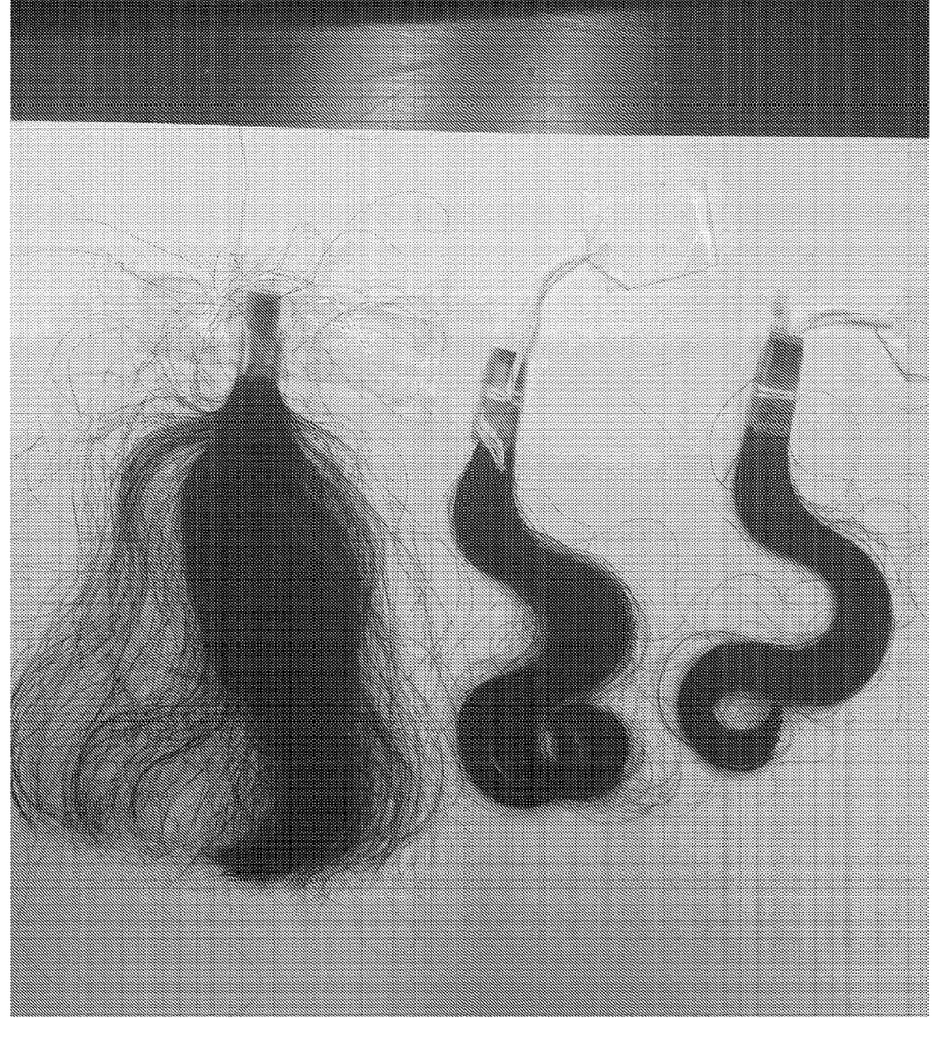
FIG. 1 shows a comparison of the appearance of an untreated hair tress with hair tresses treated with anti-frizz compositions following 6 hours exposure to 80% relative humidity and 80° F. (26.7° C.) for 6 hours.

FIG. 1 shows a comparison of three tresses of substantially identical curly hair (Brazilian) [International Hair Importers; 8729 Myrtle Ave; Glendale New York 11385] identically shampooed and blotted dry, and then treated in different ways.

The tress to the left in FIG. 1 was left untreated.

The middle tress in FIG. 1 was treated with 50 μl of a composition containing the following ingredients in the following weight percentages: 85% dimethicone (1.5 cSt); 5% propoxytetramethyl piperidinyl dimethicone; 5% dimethicone gum and 5% trimethylsiloxysiloxane.

The rightmost tress in FIG. 1 was treated with 50 μl of a composition containing the following ingredients in the following weight percentages: 72.5% dimethicone (1.5 cSt); 14.17% propoxytetramethyl piperidinyl dimethicone and 13.33% trimethylsiloxysiloxane.

For each treated tress the composition was hand-applied to the tress from the root end down. The test formulation was distributed as evenly as possible along the hair. After application of these compositions to the treated tresses all three tresses were hung in a humidifying chamber at 80% relative humidity and 80° F. for 6 hours before being photographed.

Unlike the untreated tress, which comprises a mass of single, unaligned curly hair strands, both treated tresses show a clear natural curl, in which the hair strands are well aligned. The middle tress has a soft natural feel, and the hair alignment is uncompacted, soft and natural. The rightmost tress, which shows the best natural curl definition, was somewhat stiffer with a tight hair alignment, and held its shape somewhat better than the middle tress.

Although aspects of the present invention have been described with reference to the disclosed embodiments, one skilled in the art will readily appreciate that the specific examples disclosed are only illustrative of these aspects and in no way limit the present invention. Various modifications can be made without departing from the spirit of the present invention. Each and every feature described herein, and each and every combination of two or more of such features, is included within the scope of the present invention provided that the features included in such a combination are not mutually inconsistent. Furthermore, any composition or apparatus of the invention will be understood to comprise, consist essentially of, or consist of one or more element of a claim, and additionally, each and every element not specifically included as an element of a claim shall be considered to have basis herein to be specifically excluded from that claim, in a negative limitation thereof.

Any and all patents, publications, or patent applications cited in this specification are hereby incorporated by reference as part of this specification in its entirety.

We claim:

1. A flowable composition lacking a detersive component comprising:
    a) at least about 2.5%, by weight as a percentage of the total mass of the flowable composition, of a polysiloxane fluid component comprising a propoxytetramethyl piperidinyl dimethicone, and
    b) a silicone-compatible, cosmetically acceptable, volatile liquid carrier component;
wherein said flowable composition provides at least an 80% reduction in hair frizz when frizzy hair is contacted with the flowable composition and subsequently maintained at 80° F. and 80% humidity for 6 hours, as compared to frizzy hair otherwise identically treated but not contacted with said polysiloxane fluid component comprising a propoxytetramethyl piperidinyl dimethicone.

2. The composition of claim 1 wherein said polysiloxane fluid component further comprises an amodimethicone component.

3. The composition according to claim 1 wherein the silicone-compatible, volatile liquid carrier comprises a component selected from the group consisting of: a volatile siloxy component; a volatile hydrocarbon; and a volatile alcohol.

4. The composition of claim 3 wherein the volatile siloxy component comprises a low molecular weight component selected from one or more of: a dimethicone, a dimethiconol, a phenyl methicone, a phenyl methiconol, a phenyl trimethicone, a diphenyl dimethicone, a phenyl dimethicone, a diphenylsiloxy phenyl trimethicone, a hexamethylsiloxane, a disiloxane, a trisiloxane, cyclotetrasiloxane, cyclopentasiloxane, cyclohexasiloxane.

5. The composition according to claim 1 which further comprises:
    (c) a non-volatile component comprising a component selected from the group consisting of a dimethicone component and a phenyl silicone component.

6. The composition according to claim 1 which further comprises one or more components selected from the group consisting of a colorant component, a hair shine ingredient, a sunscreen ingredient, an aesthetic modifier component, an essential oil component, a botanical component, a scent component, a nucleic acid component, a specialty extract component and a vitamin.

7. The composition of claim 1 wherein said silicone-compatible, volatile liquid carrier component comprises a volatile component selected from the group consisting of a dimethicone, a dimethiconol, a phenyl methicone, a phenyl methiconol, a phenyl trimethicone, a diphenyl dimethicone, a phenyl dimethicone, and a diphenylsiloxy phenyl trimethicone, a hexamethylsiloxane, a disiloxane, a trisiloxane, cyclotetrasiloxane, cyclopentasiloxane, cyclohexasiloxane, and a mixture of two or more of these components.

8. The composition of claim 1 wherein the composition is anhydrous.

9. A flowable anhydrous composition lacking a detersive component comprising:
    a) at least about 2.5%, by weight as a percentage of the total mass of the flowable anhydrous composition, of a polysiloxane fluid component comprising a propoxytetramethyl piperidinyl dimethicone,
    b) a silicone-compatible, volatile liquid carrier component, and
    c) a non-volatile component comprising a component selected from the group consisting of a dimethicone component, and a phenyl silicone component;
    wherein the flowable anhydrous composition provides at least an 80% reduction in hair frizz when frizzy hair is contacted with the flowable composition and subsequently maintained at 80° F. and 80% humidity for 6 hours, as compared to frizzy hair otherwise identically treated but not contacted with said polysiloxane fluid component comprising a propoxytetramethyl piperidinyl dimethicone.

10. The composition of claim 9 wherein said silicone-compatible, volatile liquid carrier component comprises a component selected from the group consisting of: a volatile siloxy component; a volatile hydrocarbon; and a volatile alcohol.

11. A method of reducing or preventing hair fizz, comprising the steps:
    i) applying to hair the flowable composition of claim 1 b) and
    ii) distributing said composition along a plurality of hair shafts.

12. A method of reducing or preventing hair frizz, comprising the steps:
   i) applying to hair the flowable composition of claim 1, and
   ii) distributing said composition along a plurality of hair shafts.

13. The method of claim 11 wherein the silicone-compatible, volatile liquid carrier comprises a component selected from the group consisting of a volatile siloxy component, a volatile hydrocarbon and a volatile alcohol.

14. The method of claim 11 wherein the silicone-compatible, volatile liquid carrier comprises a low molecular weight, volatile siloxy component.

15. The method of claim 11 wherein the polysiloxane fluid component further comprises an amodimethicone.

16. The method of claim 15 wherein said amodimethicone comprises a component selected from the group consisting of: a trimethyl silylamodimethicone component and an aminopropyl dimethicone component.

17. A flowable anhydrous composition lacking a detersive component comprising
   a) at least about 2.5%, by weight as a percentage of the total mass of the flowable anhydrous composition, of a polysiloxane fluid component comprising a propoxytetramethyl piperidinyl dimethicone,
   b) one or more silicone-compatible, non-aqueous volatile carrier, and
   c) at least one component selected from the group consisting of:
      i. at least about 5%, by weight as a percentage of the total mass of the flowable anhydrous composition, of a dimethicone component having a viscosity of greater than 150,000 cSt, and
      ii. at least about 5%, by weight as a percentage of the total mass of the flowable anhydrous composition, of an alkyl siloxysilicate;
   wherein said flowable anhydrous composition provides at least an 80% reduction in hair fizz when frizzy hair is contacted with the flowable composition and subsequently maintained at 80° F. and 80% humidity for 6 hours, as compared to frizzy hair otherwise identically treated but not contacted with said polysiloxane fluid component comprising a propoxytetramethyl piperidinyl dimethicone.

\* \* \* \* \*